US005756811A

United States Patent [19]

Assercq et al.

[11] Patent Number: 5,756,811
[45] Date of Patent: May 26, 1998

[54] PROCESS FOR THE PREPARATION OF O-CHLOROMETHYL-PHENYLGLYOXYLIC ACID DERIVATIVES

[75] Inventors: Jean-Marie Assercq, Monthey, Switzerland; Hans-Dieter Schneider, Weil am Rhein, Germany; Albert Pfiffner, Bülach; Werner Pfaff, Sisseln, both of Switzerland

[73] Assignee: Novartis Corporation, Summit, N.J.

[21] Appl. No.: 774,470

[22] Filed: Dec. 30, 1996

[30] Foreign Application Priority Data

Jan. 3, 1996 [CH] Switzerland ............... 1/96
May 2, 1996 [CH] Switzerland ............ 1112/96
Jul. 26, 1996 [CH] Switzerland ............ 1874/96

[51] Int. Cl.$^6$ ............................. C07C 229/30
[52] U.S. Cl. ....................... 560/35; 560/38; 560/60
[58] Field of Search ................... 560/35, 38, 60

[56] References Cited

U.S. PATENT DOCUMENTS

| | | | |
|---|---|---|---|
| 5,089,528 | 2/1992 | Wingert et al. | 514/640 |
| 5,116,866 | 5/1992 | Wenderoth | 514/522 |
| 5,315,025 | 5/1994 | Bushell et al. | 560/60 |
| 5,468,717 | 11/1995 | Wenderoth et al. | 504/130 |
| 5,583,249 | 12/1996 | Pfifner | 560/35 |

FOREIGN PATENT DOCUMENTS

| | | |
|---|---|---|
| 6109194 | 7/1995 | Australia . |
| 2104806 | 3/1994 | Canada . |
| 2179418 | 7/1995 | Canada . |
| 2182529 | 8/1995 | Canada . |
| 2192594 | 12/1995 | Canada . |
| 0178826 | 4/1986 | European Pat. Off. . |
| 0585751 | 3/1994 | European Pat. Off. . |
| 4305502 | 8/1994 | Germany . |
| 9518789 | 7/1995 | WIPO . |
| 9521153 | 8/1995 | WIPO . |
| 9534526 | 12/1995 | WIPO . |

*Primary Examiner*—C. Warren Ivy
*Assistant Examiner*—Charanjit S. Aulakh
*Attorney, Agent, or Firm*—Hesna J. Pfeiffer; Michael P. Morris

[57] ABSTRACT

There is described a process for the preparation of a compound of formula I

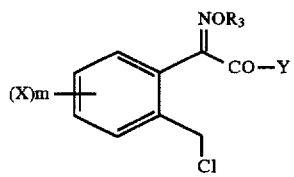

in which process:

a) a compound of formula II

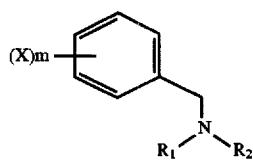

is reacted with an organolithium compound of formula III

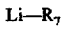 (III)

b) the resulting lithium complex is reacted with a compound of formula IV

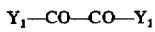

IV to form a compound of formula V

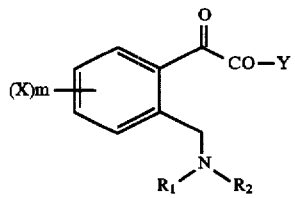

c) that compound is, in either order,
   c1) oximated with O-methylhydroxylamine; or oximated with hydroxylamine and then methylated or fluoromethylated or difluoromethylated;
   c2) reacted with a chloroformic acid ester.

X, m, Y, $R_1$ to $R_3$ and $R_7$ are as defined in the description.

14 Claims, No Drawings

PROCESS FOR THE PREPARATION OF O-CHLOROMETHYL-PHENYLGLYOXYLIC ACID DERIVATIVES

PROCESS FOR THE PREPARATION OF O-CHLOROMETHYL-PHEYLGLYOXYLIC ACID DERIVATIVES

The invention relates to a process for the preparation of a compound of formula I

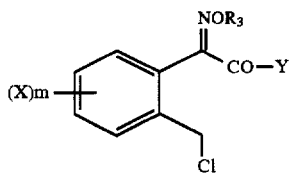

wherein:

X is a radical that is inert for the reactions;

m is from 0 to 4;

$R_3$ is hydrogen, $CH_3$, $CH_2F$ or $CHF_2$;

Y is a group $OR_4$, $N(R_5)_2$ or $N(CH_3)OCH_3$;

$R_4$ and $R_5$ are each independently of the other hydrogen or $C_1$–$C_8$alkyl; or $(R_5)_2$ together with the nitrogen atom to which they are bonded form a 5- or 6-membered, unsubstituted or substituted ring;

in which process a) a compound of formula II

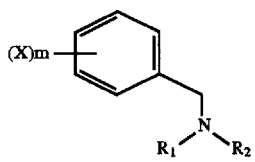

wherein

X and m are as defined for formula I, and $R_1$ and $R_2$ are each independently of the other $C_1$–$C_6$alkyl, $C_1$–$C_6$alkenyl, $C_1$–$C_6$alkoxyalkyl or $C_3$–$C_6$cycloalkyl, or $R_1$ and $R_2$ together with the nitrogen atom form an unsubstituted or substituted 6- or 7-membered ring that may contain a further nitrogen atom in addition to the nitrogen atom, is reacted, in an aprotic solvent, with an organolithium compound of formula III

     (III)

wherein $R_7$ is an organic anionic radical;

b) the resulting lithium complex is reacted with a compound of formula IV

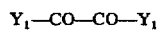     IV wherein each of the substituents $Y_1$, which may be the same or different, is a group $OR_4$, $N(R_6)_2$ or $N(CH_3)OCH_3$ or imidazole or halogen;

$R_4$ is $C_1$–$C_8$alkyl;

$R_6$ is $C_1$–$C_8$alkyl; or $(R_6)_2$ together with the nitrogen atom to which they are bonded form a 5- or 6-membered, unsubstituted or substituted ring;

and then, when $Y_1$ is imidazole or halogen, that group is replaced by Y, wherein Y is as defined for formula I; to form a compound of formula V

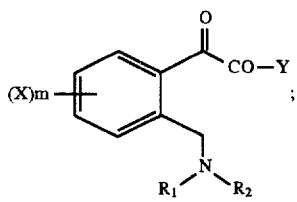

c) that compound is, in either order, c1) oximated with O-methylhydroxylamine; or oximated with hydroxylamine and then methylated or fluoromethylated or difluoromethylated;

c2) reacted with a chloroformic acid ester.

The compounds of formula I are important intermediates in the preparation of microbicides of the methoximinophenylglyoxylic acid ester series, as are described, for example, in EP 254 426, WO 95/18789 and WO 95/21153.

Unless indicated to the contrary, the above-mentioned terms have the following meanings:

The radical X may be selected as desired, provided that it is inert towards the reaction conditions, for example alkyl, alkenyl, phenyl, benzyl, nitro or alkoxy; m is preferably 0.

Depending on the number of carbon atoms, alkyl groups are straight-chained or branched and are, for example, methyl, ethyl, n-propyl, isopropyl, n-butyl, sec-butyl, isobutyl, tert-butyl, sec-amyl, tert-amyl, 1-hexyl or 3-hexyl.

Alkenyl is to be understood as being straight-chained or branched alkenyl, for example allyl, methallyl, 1-methylvinyl or but-2-en-1-yl. Alkenyl radicals having a chain length of 3 or 4 carbon atoms are preferred.

Halogen, or halo, is fluorine, chlorine, bromine or iodine, preferably fluorine, chlorine or bromine.

Haloalkyl may contain identical or different halogen atoms, for example fluoromethyl, difluoromethyl, difluorochloromethyl, trifluoromethyl, chloromethyl, dichloromethyl, trichloromethyl, 2,2,2-trifluoroethyl, 2-fluoroethyl, 2-chloroethyl, 2,2,2-trichloroethyl and 3,3,3-trifluoropropyl.

Alkoxy is, for example, methoxy, ethoxy, propyloxy, isopropyloxy, n-butyloxy, isobutyloxy, sec-butyloxy and tert-butyloxy, preferably methoxy and ethoxy. Cycloalkyl is cyclopropyl, cyclobutyl, cyclopentyl or cyclohexyl.

It is known from Organic Reactions, 26, pages 1 ff (1979) that tert-benzylamines can be lithiated in the ortho position by an organolithium compound and the latter can be substituted in the ortho position by an electrophile. That citation does not, however, mention oxalic acid derivatives as electrophiles.

Furthermore, EP-A-178 826, pages 48–75, describes in general terms that phenyllithium compounds can be reacted with oxalic acid esters to form phenylglyoxylic acid esters; in the Examples, however, no phenyllithium compounds substituted in the ortho position by an amino group are prepared; moreover, a mixture of butyllithium and potassium tert-butoxide is used for the metallation. It has now been found that benzylamines of formula II can be reacted with an organolithium compound and then with an oxalic acid derivative of formula IV to form phenylglyoxylic acid esters of formula V.

Moreover, it is known that tert-benzylamines can be converted into the corresponding benzyl chlorides by means of a chloroformic acid ester. For example, in Indian Journal of Chemistry, Vol. 31B, p. 626 (1992), an o-hydroxybenzyl-diethylamine is reacted with chloroformic acid ethyl ester to form the corresponding benzyl chloride. It has also been found that an analogous reaction can be carried out with a good yield also using benzylamines that carry a 1,2-dioxo or 1-ketoximino-2-oxo group in the ortho position, that group being retained, which is surprising given the reactivity of that functional group.

The process according to the invention makes available a novel method of synthesis for microbicides of the methoximino-phenylglyoxylic acid ester series of formula IX, as are described, for example, in EP 254 426, WO 95/18789 and WO 95/21153, which method of synthesis is distinguished by ready availability of the starting materials, good yields in the individual stages and good technical feasibility of the individual reaction steps.

That novel method of synthesis is illustrated in Reaction scheme 1.

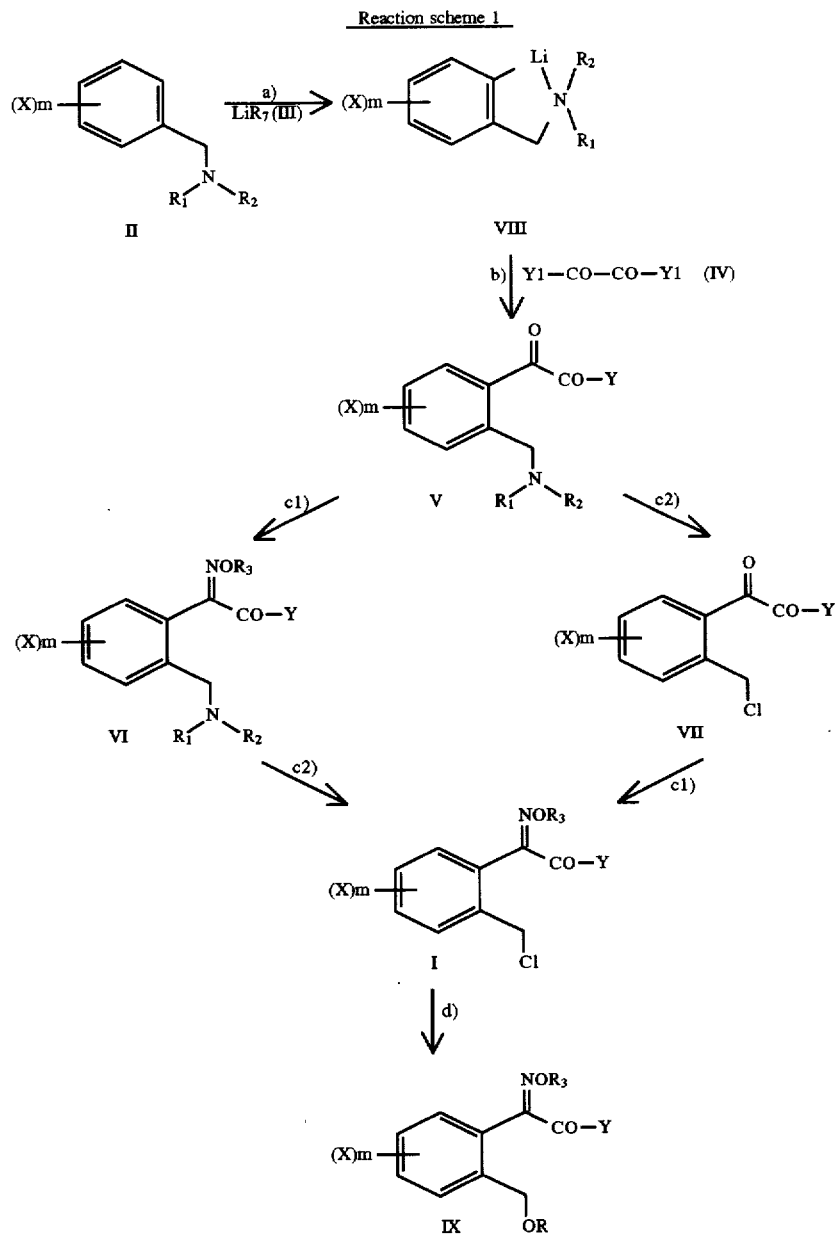

The individual reaction steps are preferably carried out as follows:

Reaction step a)

Reaction temperature from 0° to 120° C., preferably from 20° C. to the boiling point of the solvent.

The organolithium compound of formula III is butyllithium, sec-butyllithium, hexyllithium, lithium diisopropylamide (LDA), lithium hexamethyldisilazide or lithium tetramethylpiperidide (LTMP); butyllithium is especially preferred. There are advantageously used from 0.5 to 1.5 mol equivalents of the organolithium compound, based on the compound of formula II. There are preferably used as starting materials compounds of formula II wherein m is 0, and $R_1$ and $R_2$ are $C_1$–$C_6$alkyl, or $R_1$ and $R_2$ together with the nitrogen atom form piperidine.

Reaction step b)

Reaction temperature from −50° C. to the boiling point of the solvent; preferably from −20° to 30° C.

There are used from 0.9 to 4 mol equivalents of the oxalic acid derivative of formula IV, based on the compound of formula II. The oxalic acid derivative, especially an ester, may also be used as solvent.

Suitable solvents for reaction steps a) and b) are an ether or a hydrocarbon or a mixture thereof, especially hexane, benzene, toluene, xylene, tetrahydrofuran, diethyl ether, methyl tert-butyl ether, diisopropyl ether, dimethoxyethane, diethoxyethane and diethoxymethane. The two reaction steps are preferably carried out in the same solvent mixture.

Where $Y_1$, in the oxalic acid derivative of formula IV is halogen or imidazole, the glyoxylic acid halide or imidazole derivative corresponding to formula V is reacted with $HOR_4$ or $HN(R_5)_2$ under basic conditions to form the corresponding ester or amide. The glyoxylic acid ester can also be converted into the desired glyoxalic acid amide by aminolysis with $HN(R_5)_2$ or can be transesterified by an alcohol, in which case the ethyl ester is preferably converted into the methyl or n-pentyl ester.

The oxalic acid derivative used is preferably an ester, especially the ethyl ester.

Following reaction step b), the reaction mixture is advantageously acidified to a pH of 7 or less, for example with an aqueous acid, such as hydrochloric acid, sulfuric acid or phosphoric acid, or with an anhydrous acid, for example a carboxylic acid, such as propionic acid or acetic acid, or with an ammonium salt; the organic phase is then washed thoroughly with water and the product of formula V is purified by distillation or crystallisation. The product can also be purified by acid extraction of the by-products. It is also possible for reaction step b) to be followed directly by reaction step c1) or c2) without purification of the intermediate V.

Reaction step c1)

The compound of formula V is either reacted with O-methylhydroxylamine or oximated with hydroxylamine or with a salt thereof, for example the hydrochloride or sulfate, and then methylated, for example with methyl iodide, methyl chloride or dimethyl sulfate; or fluoromethylated with $BrCH_2F$; or difluoromethylated with $ClCHF_2$ under basic conditions.

Reaction step c2)

It is preferred to use chloroformic acid ethyl ester for the replacement of the amino group by chlorine.

The reaction can be carried out in an anhydrous, aprotic solvent or without a solvent, it also being possible to use a chloroformic acid ester as solvent. Preferred solvents are hydrocarbons, halogenated hydrocarbons, esters, ethers, ketones, nitrites or a chloroformic acid ester, especially benzene, toluene, xylene, chlorobenzene, nitrobenzene, petroleum ether, hexane, cyclohexane, dichloromethane, trichloromethane, dichloroethane, trichloroethane or chloroformic acid ethyl ester, more especially ethyl acetate, tert-butyl methyl ether, methyl isobutyl ketone and acetonitrile. The reaction temperature is preferably from 0° C. to the boiling point of the solvent, especially from 20° to 120° C.

In certain cases it is advantageous to carry out the reaction in the presence of a base, which is used, for example, in an amount of from 1 to 50 mol %, based on the compound of formula V. Preferred bases are alkali metal or alkaline earth metal hydrogen carbonates or carbonates.

The chloroformic acid ester can be used in any desired excess and the unreacted portion can be recovered; it is advantageous to use an amount of from 100 to 200 mol %, based on the compound of formula V.

The alcohol moiety of the chloroformic acid ester may be selected as desired, provided that it does not enter into any undesired reactions; advantageously it has not more than 8 carbon atoms, preference being given to an optionally halogenated $C_1$–$C_4$alkyl ester, an optionally halogenated $C_1$–$C_4$alkenyl ester or an unsubstituted or substituted benzyl or phenyl ester, with chloroformic acid ethyl ester being especially preferred.

$R_1$ and $R_2$ are preferably $C_1$–$C_6$alkyl, or $R_1$ and $R_2$ together with the nitrogen atom form piperidine, piperazine, hexahydroazepine or tetrahydroisoquinoline, especially piperidine.

When an amine having two amino groups, for example piperazine, is employed, both amino groups can be used for the reaction, that is to say in that case only half a mol equivalent of the amine is required.

Suitable bases are, for example, alkali metal or alkaline earth metal hydroxides, hydrides, amides, alkanolates or carbonates, dialkylamides or alkylsilylamides, alkylamines, alkylenediamines, N-unsubstituted or N-alkylated, saturated or unsaturated cycloalkyl-amines, basic heterocycles, ammonium hydroxides and also carbocyclic amines. There may be mentioned by way of example sodium hydroxide, hydride, amide, methanolate and carbonate, potassium tert-butanolate and carbonate, lithium diisopropylamide, potassium bis(trimethylsilyl)amide, calcium hydride, triethylamine, triethylenediamine, cyclohexylamine, N-cyclohexyl-N,N-dimethyl-amine, N,N-diethylaniline, pyridine, 4-(N,N-dimethylamino)-pyridine, N-methylmorpholine, benzyl-trimethyl-ammonium hydroxide and also 1,8-diaza-bicyclo[5.4.0]undec-5-ene (DBU).

Reaction step d)

The compound of formula I is reacted with a compound of the formula HOR, wherein R is an organic radical, under basic conditions in a solvent according to known methods. The resulting compound of formula IX may, if desired, when Y is a group $OR_4$, be transesterified or amidated according to generally known methods.

In reaction step d) it is especially preferred to react a compound of formula I wherein m is 0, $R_3$ is methyl and Y is methoxy or ethoxy with a compound of formula A1 or A2

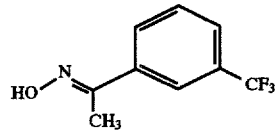

A1

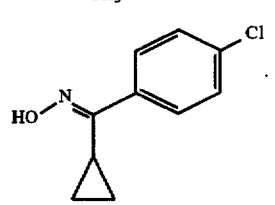

A2

In the transesterification, a $C_2$–$C_8$alkyl ester, especially the ethyl ester, is preferably converted into the corresponding methyl ester with methanol.

The reactions can also be carried out with phase transfer catalysis in an organic solvent, for example methylene chloride or toluene, in the presence of an aqueous basic solution, for example sodium hydroxide solution, and a phase transfer catalyst, for example tetrabutylammonium hydrogen sulfate.

Typical reaction conditions will be found in the Examples.

The invention relates also to a process for the preparation of a compound of formula V

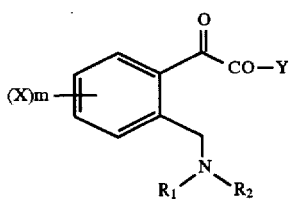

wherein

X is a radical that is inert for the reaction;

m is from 0 to 4;

$R_1$ and $R_2$ are each independently of the other $C_1$–$C_6$alkyl, $C_1$–$C_6$alkenyl, $C_1$–$C_6$alkoxyalkyl or $C_3$–$C_6$cycloalkyl; or $R_1$ and $R_2$ together with the nitrogen atom form an unsubstituted or substituted 6- or 7-membered ring that may contain a further nitrogen atom in addition to the nitrogen atom, Y is a group $OR_4$, $N(R_5)_2$ or $N(CH_3)OCH_3$;

$R_4$ and $R_5$ are each independently of the other hydrogen or $C_1$–$C_8$alkyl; or $(R_5)_2$ together with the nitrogen atom to which they are bonded form a 5- or 6-membered, unsubstituted or substituted ring; in which process a) a compound of formula II

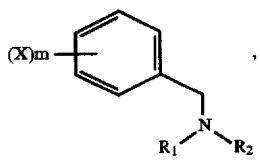

wherein X, m, $R_1$ and $R_2$ are as defined for formula V, is reacted, in an aprotic solvent, with an organolithium compound of formula III

   (III)

wherein $R_7$ is an organic anionic radical;

b) the resulting lithium complex is reacted with a compound of formula IV

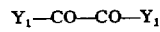   IV wherein each of the substituents $Y_1$, which may be the same or different, is a group $OR_4$, $N(R_6)_2$ or $N(CH_3)OCH_3$ or imidazole or halogen;

$R_4$ is $C_1$–$C_8$alkyl;

$R_6$ is $C_1$–$C_8$alkyl; or $(R_6)_2$ together with the nitrogen atom to which they are bonded form a 5- or 6-membered, unsubstituted or substituted ring;

and then, when $Y_1$ is imidazole or halogen, that group is replaced by Y, wherein Y is as defined for formula I; to form a compound of formula V.

The invention relates also to a process for the preparation of a compound of formula I

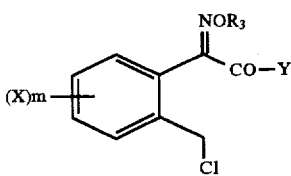

wherein:

X is a radical that is inert for the reactions;

m is from 0 to 4;

$R_3$ is hydrogen, $CH_3$, $CH_2F$ or $CHF_2$;

Y is a group $OR_4$, $N(R_5)_2$ or $N(CH_3)OCH_3$;

$R_4$ and $R_5$ are each independently of the other hydrogen or $C_1$–$C_8$alkyl; or $(R_5)_2$ together with the nitrogen atom to which they are bonded form a 5- or 6-membered, unsubstituted or substituted ring;

in which process a compound of formula V

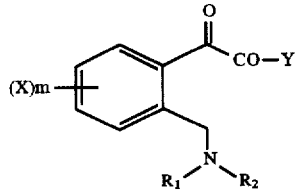

wherein X, m and Y are as defined for formula I and $R_1$ and $R_2$ are each independently of the other $C_1$–$C_6$alkyl, $C_1$–$C_6$alkenyl, $C_1$–$C_6$alkoxyalkyl or $C_3$–$C_6$cycloalkyl, or $R_1$ and $R_2$ together with the nitrogen atom form an unsubstituted or substituted 6- or 7-membered ring that may additionally contain a further nitrogen atom, is, in either order, c1) oximated with O-methylhydroxylamine; or oximated with hydroxylamine and then methylated or fluoromethylated or difluoromethylated;

c2) reacted with a chloroformic acid ester.

The invention relates also to the novel compounds of formulae V and VII

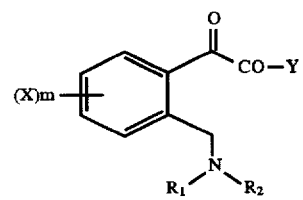

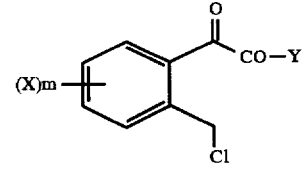

wherein:

X is a radical that is inert for the reactions;

m is from 0 to 4;

Y is a group $OR_4$, $N(R_5)_2$ or $N(CH_3)OCH_3$;

$R_4$ and $R_5$ are each independently of the other hydrogen or $C_1$–$C_8$alkyl; or $(R_5)_2$ together with the nitrogen atom to which they are bonded form a 5- or 6-membered, unsubstituted or substituted ring;

R₁ and R₂ are each independently of the other $C_{1-C_6}$alkyl, $C_{1-C_6}$alkenyl, $C_{1-C_6}$alkoxyalkyl or $C_3-C_6$cycloalkyl, or R₁ and R₂ together with the nitrogen atom form an unsubstituted or substituted 6- or 7-membered ring that may contain a further nitrogen atom in addition to the nitrogen atom.

Preference is given to compounds wherein m is 0;

Y is a group OR₄;

R₄ is $C_{1-C_8}$alkyl, especially ethyl;

R₁ and R₂ are each independently of the other $C_1-C_6$alkyl, especially methyl, or R₁ and R₂ together with the nitrogen atom form piperidine.

Particularly preferred are the compounds Vb and VIIb

Vb

VIIb

The invention relates also to compounds of formula I

I wherein:

X is a radical that is inert for the reactions;

m is from 0 to 4;

R₃ is hydrogen, CH₃, CH₂F or CHF₂;

Y is a group OR₄, N(R₅)₂ or N(CH₃)OCH₃;

R₄ is $C_2-C_4$alkyl; the substituents R₅ are each independently of the other hydrogen or $C_1-C_8$alkyl; or (R₅)₂ together with the nitrogen atom to which they are bonded form a 5- or 6-membered, unsubstituted or substituted ring;

preferably those wherein m is 0;

R₃ is CH₃;

Y is a group OR₄; and

R₄ is $C_2-C_4$alkyl, especially ethyl.

The invention relates also to the novel compounds of the formulae

IXb

IXc

PREPARATION EXAMPLES

Abbreviations: RT= room temperature; THF= tetrahydrofuran; h= hours; min= minutes Example 1 o-(N,N-Dimethylaminomethyl)-phenylglyoxylic acid methyl ester Va

IIa                Va

Example 1.1

A solution of n-butyllithium in hexane (15%; 107.6 g; 0.25 mol) is metered, at RT, over the course of 20 min, into a solution of N-benzyldimethylamine IIa (24.1 g; 0.175 mol) in diethyl ether (60 ml), and the mixture is maintained at reflux at approximately 50° C. for 3 h; the mixture is then metered, at −50° C., into dimethyl oxalate (50.1 g; 0.42 mol) in THF (160 ml) and is heated to RT; methyl chloroformate (20.3 g; 0.21 mol) is added, the mixture is stirred at RT for 1.5 h and concentrated by evaporation in vacuo; 100 ml of each of methylene chloride and water are added to the residue and the organic phase is separated off and concentrated by evaporation. The residue is 38.1 g of product (content 80%; yield 79%).

Example 1.2

A solution of n-butyllithium in toluene (20%; 82.3 g; 0.26 mol) is metered over the course of from 10 to 15 min into a solution of N-benzyldimethylamine (24.1 g; 0.175 mol) in tert-butyl methyl ether (60 ml). The mixture is maintained at from 55° to 60° C. for 3 h, cooled to RT and added, at -50° C., to a solution of dimethyl oxalate (50.1 g; 0.42 mol) in toluene (138.7 g). The reaction mixture is heated to RT and stirred at approximately 25° C. for 13 h; methyl chloroformate (20.3 g; 0.21 mol) is added and the mixture is stirred at RT for 1 h and concentrated by evaporation in vacuo. Methylene chloride (100 ml) and water (100 ml) are added to the residue and the organic phase is separated off. The residue is 26.6 g of product (content 87%, yield 69%).

Example 1.3

A solution of n-butyllithium in hexane (15%; 89.7 g; 0.21 mol) is added over the course of from 10 to 15 min to a solution of N-benzyldimethylamine (24.1 g; 0.17 mol) in diethyl ether (60 ml), and the mixture is maintained at reflux at approximately 55° C. for 3 h. The mixture is cooled to RT and added to a solution, pre-cooled to -20° C., of methyloxalyl chloride (66.3 g; 0.52 mol) in diethyl ether (160 ml). After 30 minutes' stirring at from -10° C. to 0° C., the reaction mixture is cooled again to -20° C. and diluted with diethyl ether (100 ml). While maintaining the temperature at from -20° C. to -10° C., a solution of sodium methanolate in methanol (30%; 56.8 g; 0.31 mol) is added. The mixture is heated to RT, methylene chloride (200 ml) is added and the mixture is stirred overnight. The salts are filtered off. The concentrate is taken up in toluene (200 ml) and the salts that remain are filtered off and washed with toluene (50 ml). The filtrate yields 23.1 g of product (content 72%; yield 43.1%).

Example 1.4

A solution of n-butyllithium in hexane (15%; 52 g; 0.12 mol) is added over the course of from 10 to 15 min to a solution of N-benzyldimethylamine (13.8 g; 0.10 mol) in diethyl ether (60 ml). The resulting mixture is maintained at reflux at from 40° to 45° C. for approximately 3 h and is then cooled to RT. The mixture is then added at from -20° C. to -10° C. to a pre-prepared mixture of 31 g of triethylamine (0.30 mol) and 37.9 g of methyloxalyl chloride (0.30 mol) in 160 ml of diethyl ether. The resulting mixture is cooled to -20° C. and 32 g of methanol are added, during which the temperature rises to RT. The mixture is stirred at RT overnight, followed by filtration, washing twice with 100 ml of diethyl ether and concentration by evaporation in vacuo. The residue is dissolved in 100 ml of methylene chloride and 50 ml of water, and the organic phase is separated off and concentrated by evaporation: 16.4 g of product (content 69%, yield 51%).

Example 2 o-(N,N-Dimethylaminomethyl)-phenylglyoxylic acid ethyl ester Vb

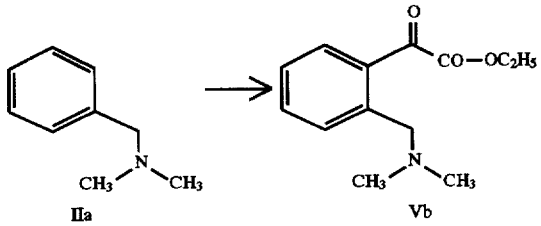

Example 2.1

A solution of n-butyllithium in hexane (15%; 183.8 g; 0.43 mol) is added over the course of 15 min to a solution of 48.3 g of N-benzyldimethylamine (0.35 mol) in 120 ml of methyl tert-butyl ether. The mixture is heated at from 50° to 55° C. for 4 h and then, over the course of 30 min, is metered into a cold (-20° C.) suspension of 124 g of diethyl oxalate (0.84 mol) in 320 ml of methyl tert-butyl ether. The reaction mixture is then heated to RT, and acetic acid (100%; 25.2 g; 0.42 mol) and then a mixture of 100 g of crushed ice and 200 g of water are added. The phases are separated and the organic phase is washed with 100 ml of water and concentrated by evaporation in vacuo: 78 g (content 86.4%; yield 82%).

Example 2.2

The procedure is the same as in the preceding Example, but butyllithium in toluene (20%) is used instead of butyllithium in hexane. Yield: 72 g (content 84.8%; yield 74%).

Example 2.3

A solution of n-butyllithium in hexane (15%; 54.2 g; 0.13 mol) is added over the course of from 10 to 15 min to a solution of 13.8 g of N-benzyldimethylamine (0.10 mol) in 60 ml of diethyl ether, and the mixture is maintained at reflux at from 35° to 45° C. for 3 h. The reaction mixture is cooled to RT and is metered, over the course of 5 min, into a pre-cooled (-20° C.) solution of 42.2 g of ethyloxalyl chloride (0.30 mol) in 160 ml of diethyl ether. The reaction mixture is stirred at 30° C. for 30 min and then cooled to -20° C. At from -20° C. to 0° C., 46 g of ethanol (1.0 mol) and 36.4 g of triethylamine (0.35 mol) are added in succession. The reaction mixture is then heated to RT and stirred for 1 h, and the salts are filtered off and washed with 3×50 ml of diethyl ether. The combined filtrates are concentrated by evaporation in vacuo. The residue is dissolved in 200 ml of methylene chloride and 50 ml of water, and the organic phase is separated off and concentrated by evaporation:19.3 g (content 77%; yield 63%).

Example 3 o-(N,N-Dimethylaminomethyl)-phenylglyoxylic acid n-pentyl ester Vc

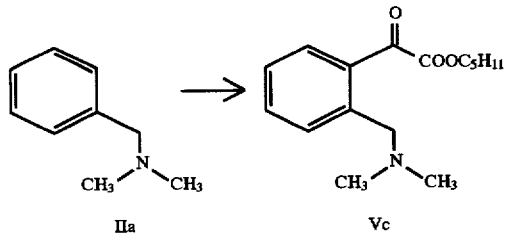

Example 3.1

The procedure is the same as in Example 1.1, but di-n-pentyl oxalate is used instead of dimethyl oxalate. Yield: 62%.

Example 3.2

A solution of n-butyllithium in hexane (15%; 92.7 g; 0.22 mol) is added over the course of from 10 to 15 min to a solution of 24.1 g of N-benzyldimethylamine (0.175 mol) in 60 ml of diethyl ether, and the mixture is maintained at reflux at from 50° to 55° C. for approximately 3 h. The mixture is cooled to RT and is added over the course of 5 min to a pre-cooled (-20° C.) solution of 93.8 g of n-pentyloxalyl chloride (0.52 mol) in 160 ml of diethyl ether, and the mixture is stirred for 30 min, during which time the temperature is allowed to rise to 30° C. At from −20° C. to 0° C., a mixture of 10 g of methanol (0.31 mol) and 32.5 g of triethylamine (0.31 mol) is added, the reaction mixture is then stirred at RT overnight and concentrated by evaporation in vacuo, and the residue is taken up in 200 ml of methylene chloride and 150 ml of water. The organic phase is separated off and concentrated by evaporation: 98.5 g (content 32%; yield 65%).

Example 4 o-Chloromethyl-phenylglyoxylic acid methyl ester VIIa

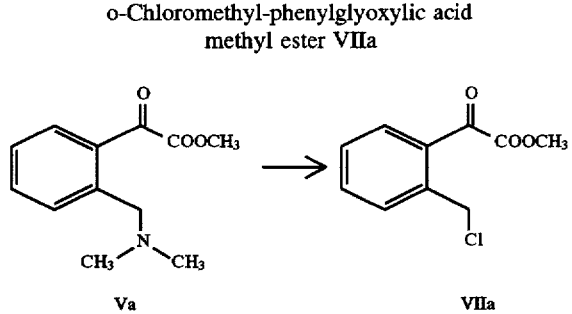

15.9 g of methyl chloroformate (165 mmol) are added at from 20° to 25° C. to a solution of 18.3 g of o-(N,N-dimethylaminomethyl)-phenylglyoxylic acid methyl ester Va (content 88.6%; 73.3 mol) in 100 ml of toluene. The reaction mixture is stirred at RT overnight, heated at 60° C. for 1 h, cooled and concentrated by evaporation in vacuo. 15.3 g (content 83%; yield 82%) of product are obtained.

Example 5 o-Chloromethyl-phenylglyoxylic acid ethyl ester VIIb

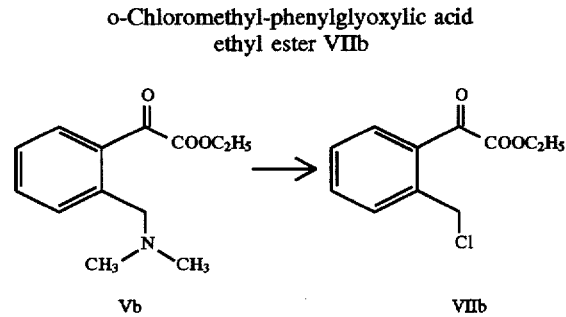

11.5 g of methyl chloroformate (119 mmol) are added at from 20° to 25° C. to a solution of 10.3 g of (N,N-dimethylaminomethyl)-phenylglyoxylic acid ethyl ester Vb (content 91.3%; 40 mmol) in 40 ml of toluene. Stirring is carried out at RT overnight. The reaction mixture is concentrated by evaporation in vacuo to yield 10.1 g (content 85%; yield 94%) of product.

Example 6 o-(N,N-Dimethylaminomethyl)-phenylglyoxylic acid methyl ester O-methyloxime

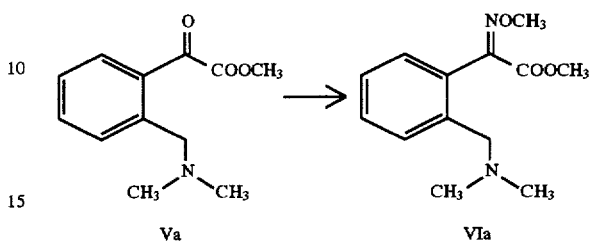

14.4 g of keto ester Va (content 72%; 46.9 mmol) are added to a mixture of 4.2 g of O-methylhydroxylamine hydrochloride (49.3 mmol), 100 g of toluene, 20 ml of methanol and 0.4 g of p-toluenesulfonic acid. The reaction mixture is heated at from 50° to 55° C. for 10 h and then concentrated by evaporation In vacuo. The resulting salts are dissolved in 100 ml of methylene chloride and 8 g of sodium carbonate, the salts are filtered off and the solution is concentrated by evaporation in vacuo. 11.9 g (content 82%, yield 83%) of product are obtained.

Example 7 o-Chloromethyl-phenylglyoxylic acid n-pentyl ester O-methyloxime Ic

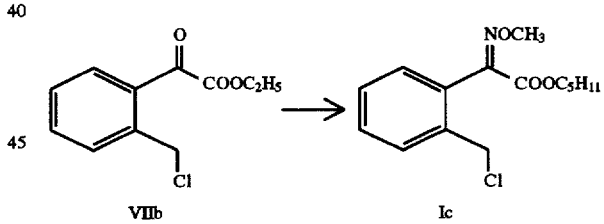

A solution of 10.1 g of keto ester VIIb (approximately 80%; 36 mmol) and p-toluenesulfonic acid monohydrate (0.18 g; mmol) in 39 g of n-pentanol is heated at from 90° to 95° C. for 4 h. Approximately 6 g of solvent are then distilled off and replaced by pentanol, and the reaction is completed. After cooling to RT, 3.7 g of methoxylamine hydrochloride (44.5 mmol) are added and the reaction mixture is stirred at 60° C. for 20 h, cooled to RT and added to a mixture of 60 g of ice and 40 g of water. The resulting mixture is neutralised with aqueous NaHCO₃, and the organic phase is separated off, washed with 30 ml of water and concentrated by evaporation in vacuo. 10.3 g of crude product are obtained in the form of a mixture of the pentyl ester Ic (approximately 50%) and the ethyl ester Ia (approximately 30%).

Example 8 o-Piperidinomethyl-phenylglyoxylic acid ethyl ester Ve

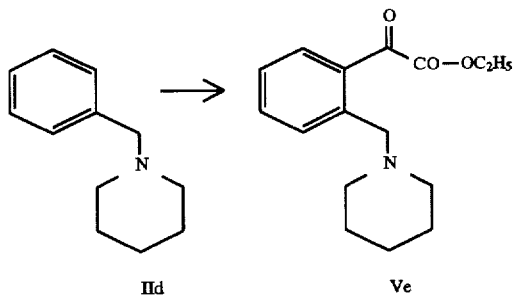

A solution of n-butyllithium in toluene (20%; 65.6 g; 0.20 mol) is added over the course of from 10 to 15 min to a solution of 31 g of N-benzylpiperidine (0.175 mol) in 60 ml of tert-butyl methyl ether. The reaction mixture is heated at from 55° to 60° C. for approximately 18 h and then metered at RT into a cold (−20° C.) solution of 50.1 g of diethyl oxalate (0.42 mol) in 160 ml of toluene. The mixture is heated to RT and stirred at from 20° to 25° C. for 30 min. Acetic acid (100%; 12.6 g; 0.21 mol) and a mixture of 50 g of crushed ice and 100 g of water are then added to the reaction mixture. The phases are separated and the organic phase is washed with 50 ml of water and concentrated by evaporation in vacuo: 43.2 g (content 89%; yield 80%).

Example 9 o-Piperidinomethyl-phenylglyoxylic acid n-pentyl ester Vf

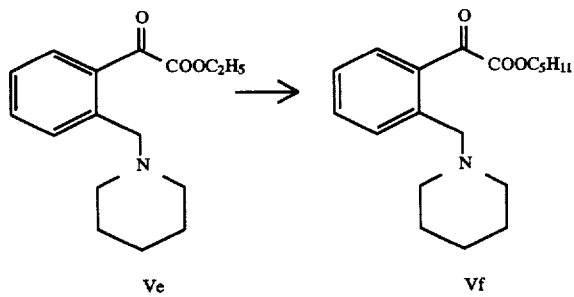

In a solution of Ve (51.8 g; 92%; 0.2 mol) and sodium methoxide (95%; 0.57 g; 10 mmol) in 180 g of n-pentanol, ethanol is distilled off continuously under reflux (from 70° to 75° C.) in vacuo (200 mbar) (reflux ratio 1:20). After approximately 2 h, the mixture is cooled to RT and poured into a mixture of 50 g of ice, 50 g of water and 0.6 g of acetic acid. The phases are separated and the organic phase is washed with 50 ml of water and concentrated by evaporation in vacuo: 59.4 g (content 86.5%; yield 98%).

Example 10

2-(α-Chloromethylphenyl)-2-methoximino-acetic acid methyl ester Ia

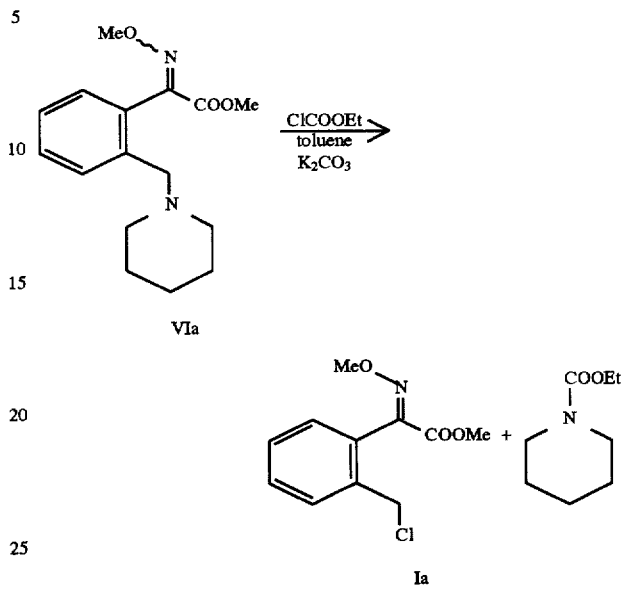

In a 100 ml sulfonating flask, 15.7 g of methoximinocarboxylic acid ester VIa (dist., 91.3%; 49.4 mmol) are dissolved in 20 ml of toluene, and 0.3 g (2.15 mmol) of powdered potassium carbonate is added. 7.1 ml of chloroformic acid ethyl ester (74.6 mmol) are then rapidly added dropwise, at RT, the temperature rising from RT to 41° C. in the course of 10 min. When the exothermic reaction has subsided, the mixture is heated to 950° C. and the conversion is determined by means of GC: 86%. A further 1.41 ml of chloroformic acid ethyl ester (14.8 mmol) are then added and after ¼ h the conversion is determined again: 98%. After a total reaction time of 1 h, the reaction mixture is cooled, poured into a brine solution and rendered weakly acidic with 1 N hydrochloric acid. Exhaustive extraction is then carried out with ethyl acetate, and working up is carried out in the customary manner.

Crude yield: 22.4 g of an orange oil.

In order to determine the yield of [E/Z] isomers precisely, chromatography is carried out on silica gel using ethyl acetate/hexane 1:6, and the carbamate that has been carried therewith (7.18 g) is distilled off under a high vacuum with gentle heating. Yield: 11.81 g, viscous yellow oil, or 99% of the theoretical yield; purity: 96.5%; total yield: 95.4% of the theoretical yield; [E/Z]-ratio (GC):=80:20.

In this Example, 4 mol % of potassium carbonate and 180 mol % of chloroformic acid ethyl ester, based on the starting material, are used.

Isomerisation:

On standing overnight, the [E] form crystallises out in the oil and can be filtered off and washed with methylcyclohexane tert-butyl methyl ether and then dried under a high vacuum to constant weight.

1st crystallisate: 6.37 g of white crystals.

5.44 g of the [E/Z] mixture from the mother liquor are dissolved while hot in 20 ml of methylcyclohexane, the solution is cooled to room temperature and a weak stream of hydrogen chloride gas is introduced for 5 h. The solution, which is initially dark violet, turns dark green and the [E] isomer precipitates out and can be filtered off.

2nd crystallisate: 3.26 g of dark green crystals
Total yield of [E] isomer: 9.63 g or 81% of the theoretical yield.

Example 11

2-(α-Chloromethylphenyl)-2-methoximino-acetic acid ethyl ester Ib

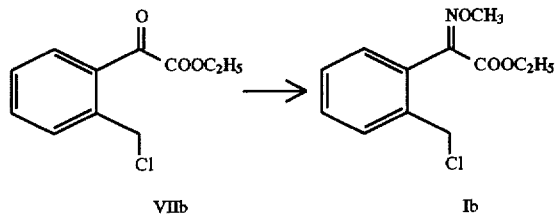

20 g of chloromethylketoethyl ester (0.071 mol) are placed in a sulfonating flask together with 6.6 g of o-methylhydroxylamine hydrochloride (0.08 mol) and 30 g of absolute ethanol, and the mixture is heated at from 50° to 55° C. After 3 hours' stirring at from 50° to 55° C., 10 g of hydrogen chloride gas (0.27 mol) are introduced at the same temperature in the course of 30 min. After stirring for 17 h at from 50° to 55° C. to complete the reaction, the reaction mixture is cooled to from 0° to 5° C. and the pH is adjusted to from 7 to 9 with sodium hydroxide solution. The resulting product is filtered off and washed three times with 10 ml of cold water each time. The moist crude product is then dried in a drying chamber in vacuo at 30° C. The product, (2-chloromethyl-phenyl)-methoxyimino-acetic acid ethyl ester, is obtained in a yield of 87% of the theoretical yield and having a content of 90.5% (consisting of: 82.8% E isomer and 7.7% Z isomer). The content of E isomer can be increased to more than 95% by recrystallisation. The melting point of the (99%) E isomer is 73° C. The Z isomer is liquid at room temperature.

Example 12

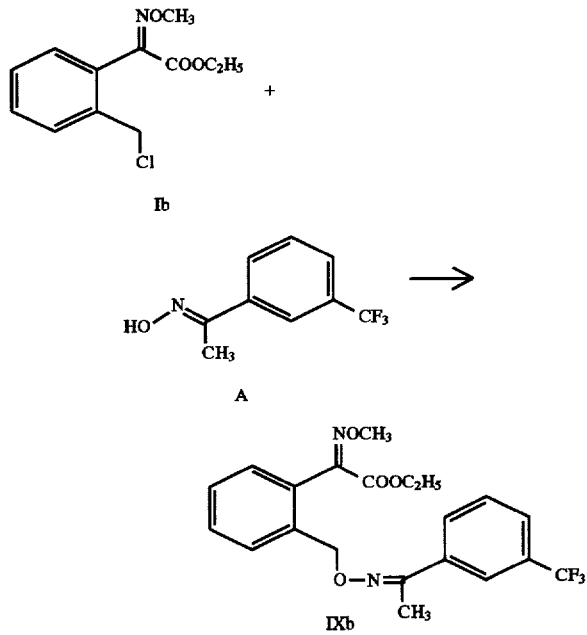

6.1 g of a 30% sodium methanolate solution in methanol are added dropwise in the course of 10 minutes to a solution of 7.0 g of 3-trifluoromethylacetophenone oxime (A) (0.034 mol) in 8 ml of dimethylacetamide. At from 55° to 70° C. and from 250 to 50 mbar, 3.5 ml of solvent are distilled off. After the addition of 0.07 g of potassium iodide, 9.25 g of 90% 2-(α-chloro-methyl-phenyl)-2-methoximino-acetic acid ethyl ester Ib (0.032 mol), dissolved in 12 ml of dimethylacetamide, are metered in at from 55° to 65° C. over the course of 20 min. After stirring for 3 hours to complete the reaction, the reaction mixture is metered at from 20° to 25° C., over the course of 30 minutes, into a mixture of 30 ml of water and 18 ml of toluene, the pH value being adjusted to from 4 to 5 with 32% hydrochloric acid. The aqueous lower phase is extracted twice with 10 ml of toluene each time. The combined organic phases are extracted with 10 ml of water. The solvent is distilled off in vacuo at 60° C. 14.8 g of crude oil of compound IXb having a content of 78% are obtained. After purification, a solid substance having a melting point of 47° C., content 95%, is obtained.

This reaction can also be carried out, for example, in DMF or N-methylpyrrolidone under the same conditions, or in acetonitrile using potassium carbonate as base.

Example 13

Transesterification

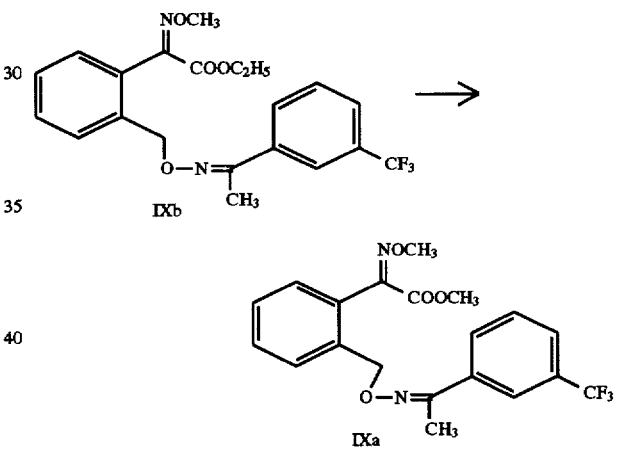

A solution of 14.8 g of the ethyl ester compound IXb (content: 78%; 0.027 mol) in 53 ml of methanol and 1.5 g of 30% sodium methanolate in methanol is stirred for 2 hours at from 40° to 45° C. The reaction mixture is metered at from 20° to 25° C. into a mixture of 53 ml of toluene, 10 ml of water and 1 g of 32% hydrochloric acid, the pH value being maintained with hydrochloric acid at from 3 to 3.5. After separation of the phases, the aqueous phase is extracted twice with 10 ml of toluene each time. The combined organic phases are extracted twice with 16 ml of water each time. After evaporation of the organic solvent in vacuo at from 60° to 65° C., 13.4 g of crude product are obtained, which are dissolved at from 55° to 60° C. in 27 ml of methylcyclohexane. During cooling to from 0° to 5° C., the product precipitates out and is filtered off and washed with methylcyclohexane at from 0 to 5° C. After drying in vacuo at 40° C., 9 g of product IXa having a melting point of 69°–71° C. are obtained.

What is claimed is:

1. A process for the preparation of a compound of formula I

19

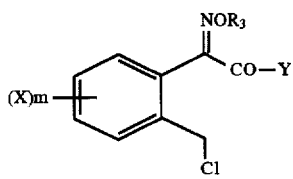

wherein:

X is a radical that is inert for the reactions;

m is from 0 to 4;

$R_3$ is hydrogen, $CH_3$, $CH_2F$ or $CHF_2$;

Y is a group $OR_4$, $N(R_5)_2$ or $N(CH_3)OCH_3$;

$R_4$ and $R_5$ are each independently of the other hydrogen or $C_1$–$C_8$alkyl; or $(R_5)_2$ together with the nitrogen atom to which they are bonded form a 5- or 6-membered, unsubstituted or substituted ring;

in which process a) a compound of formula II

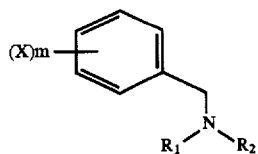

wherein

X and m are as defined for formula I, and $R_1$ and $R_2$ are each independently of the other $C_1$–$C_6$alkyl, $C_1$–$C_6$alkenyl, $C_1$–$C_6$alkoxyalkyl or $C_3$–$C_6$cycloalkyl, or $R_1$ and $R_2$ together with the nitrogen atom form an unsubstituted or substituted 6- or 7-membered ring that may contain a further nitrogen atom in addition to the nitrogen atom, is reacted, in an aprotic solvent, with an organolithium compound of formula III Li—$R_7$ (III)

wherein $R_7$ is an organic anionic radical;

b) the resulting lithium complex is reacted with a compound of formula IV $Y_1$—CO—CO—$Y_1$ IV wherein each of the substituents $Y_1$, which may be the same or different, is a group $OR_4$, $N(R_6)_2$ or $N(CH_3)OCH_3$ or imidazole or halogen;

$R_4$ is $C_1$–$C_8$alkyl;

$R_6$ is $C_1$–$C_8$alkyl; or $(R_6)_2$ together with the nitrogen atom to which they are bonded form a 5- or 6-membered, unsubstituted or substituted ring;

and then, when $Y_1$ is imidazole or halogen, that group is replaced by Y, wherein Y is as defined for formula I;

20 to form a compound of formula V

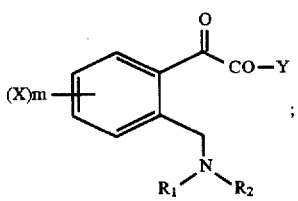

c) that compound is, in either order, c1) oximated with O-methylhydroxylamine; or oximated with hydroxylamine and then methylated or fluoromethylated or difluoromethylated;

c2) reacted with a chloroformic acid ester.

2. A process according to claim 1, wherein reaction step a) is carried out at from 0° C. to 120° C. and reaction step b) is carried out at from −50° C. to +30° C.

3. A process according to claim 1, wherein the solvent for reaction steps a) and b) is an ether or a hydrocarbon or a mixture thereof.

4. A process according to claim 3, wherein the hydrocarbon is hexane, benzene, toluene or xylene and the ether is tetrahydrofuran, diethyl ether, methyl tert-butyl ether, diisopropyl ether, dimethoxyethane, diethoxyethane or diethoxymethane.

5. A process according to claim 1, wherein the organolithium compound of formula III is butyllithium, sec-butyllithium, hexyllithium, lithium diisopropylamide (LDA), lithium hexamethyldisilazide or lithium tetramethylpiperidide (LTMP).

6. A process according to claim 5, wherein the organolithium compound of formula III is butyllithium.

7. A process according to claim 1, wherein in the compound of formula IV $Y_1$ is $OR_3$, especially $OC_2H_5$.

8. A process according to claim 1, wherein in the compound of formula II m is 0, and $R_1$ and $R_2$ are each independently of the other $C_1$–$C_6$alkyl, or $R_1$ and $R_2$ together with the nitrogen atom form piperidine.

9. A process according to claim 1, wherein in reaction step a) there are used from 0.5 to 1.5 mol equivalents of the organolithium compound of formula III, based on the compound of formula II.

10. A process according to claim 1, wherein in reaction step b) there are used from 0.9 to 4 mol equivalents of the oxalic acid derivative of formula IV, based on the compound of formula II.

11. A process according to claim 1, wherein following reaction step b) the reaction mixture is adjusted to a pH of 7 or less.

12. A process according to claim 1, wherein chloroformic acid ethyl ester is used in reaction step c2).

13. A process according to claim 1, wherein in formulae I, II and V m is 0.

14. A process for the preparation of a compound of formula I

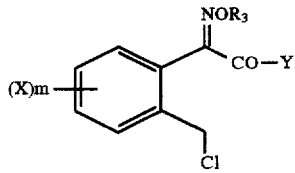   I wherein:

X is a radical that is inert for the reactions;

m is from 0 to 4;

$R_3$ is hydrogen, $CH_3$, $CH_2F$ or $CHF_2$;

Y is a group $OR_4$, $N(R_5)_2$ or $N(CH_3)OCH_3$;

$R_4$ and $R_5$ are each independently of the other hydrogen or $C_1$–$C_8$alkyl; or $(R_5)_2$ together with the nitrogen atom to which they are bonded form a 5- or 6-membered, unsubstituted or substituted ring;

in which process a compound of formula V

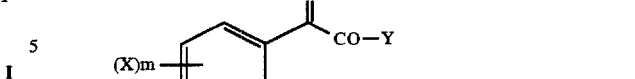   V wherein X, m and Y are as defined for formula I and $R_1$ and $R_2$ are each independently of the other $C_1$–$C_6$alkyl, $C_1$–$C_6$alkenyl, $C_1$–$C_6$alkoxyalkyl or $C_3$–$C_6$cycloalkyl, or $R_1$ and $R_2$ together with the nitrogen atom form an unsubstituted or substituted 6- or 7-membered ring that may additionally contain a further nitrogen atom, is, in either order, c1) oximated with O-methylhydroxylamine; or oximated with hydroxylamine and then methylated or fluoromethylated or difluoromethylated;

c2) reacted with a chloroformic acid ester.

* * * * *